US00PP12764P2

(12) United States Plant Patent
van Gaalen

(10) Patent No.: US PP12,764 P2
(45) Date of Patent: Jul. 9, 2002

(54) PHLOX PLANT NAMED 'SILVERMINE'

(75) Inventor: Irenaeus Antonius Maria van Gaalen, Den Hoorn (NL)

(73) Assignee: Witteman + Co.'Multiflora ' B.V., Hillegom (NL)

( * ) Notice: Subject to any disclaimer, the term of this patent is extended or adjusted under 35 U.S.C. 154(b) by 0 days.

(21) Appl. No.: 09/840,958

(22) Filed: Apr. 25, 2001

(51) Int. Cl.[7] ..... A01H 5/00
(52) U.S. Cl. ..... Plt./320
(58) Field of Search ..... Plt./320

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Phlox plant named 'Silvermine', characterized by its unique green and pale yellow variegated foliage; upright plant habit; and numerous white-colored flowers.

2 Drawing Sheets

BACKGROUND OF THE INVENTION

The present Invention relates to a new and distinct cultivar of Phlox plant, botanically known as *Phlox paniculata*, and hereinafter referred to by the cultivar name Silvermine.

The new Phlox is a naturally-occurring whole plant mutation of the *Phlox paniculata* cultivar Popeye, not patented. The new Phlox was discovered by the Inventor in a controlled environment in Den Hoorn, The Netherlands, within a population of plants of 'Popeye' in 1998. The selection of this new Phlox was based on its unique variegated foliage. Plants of the cultivar Popeye have solid green-colored foliage whereas plants of the new Phlox have variegated foliage.

Asexual reproduction of the new cultivar by vegetative cuttings taken at Den Hoorn, The Netherlands since 1999, has shown that the unique features of this new Phlox are stable and reproduced true to type in successive generations.

SUMMARY OF THE INVENTION

Plants of the cultivar Silvermine have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'Silvermine'. These characteristics in combination distinguish 'Silvermine' as a new and distinct cultivar:

1. Unique pale yellow and green variegated foliage.
2. Upright plant habit.
3. Numerous white-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Phlox.

The photograph at the top of the first sheet comprises a side perspective view of a typical flowering stem of 'Silvermine'.

The photograph at the top of the second sheet comprises a close-up view of a typical inflorescence of 'Silvermine'.

The photograph at the bottom of the second sheet comprises a close-up view of the upper surface of mature and young leaves of 'Silvermine'.

DETAILED BOTANICAL DESCRIPTION

The following observations, measurements and values describe plants of the new cultivar grown in the field under outdoor conditions during the summer in Den Hoorn, The Netherlands. Plants used in the photographs and the detailed botanical description were about 30 weeks from planting rooted cuttings. Color references are made to The Royal Horticultural Society Colour Chart except where general terms of ordinary dictionary significance are used.

Botanical classification: *Phlox paniculata* cultivar Silvermine.

Parentage: Naturally-occurring whole plant mutation of *Phlox paniculata* cultivar Popeye, not patented.

Propagation:
- *Type cutting.*—Vegetative cuttings.
- *Time to produce a rooted liner.*—About 30 days during the spring in Den Hoorn, The Netherlands.
- *Root description.*—Fine.

Plant description:
- *Form.*—Upright, conical.
- *Usage.*—Perennial garden plant.
- *Crop time.*—From cuttings, about 30 weeks are required to produce fully-grown flowering plants in 1.5-liter containers.
- *Plant height.*—About 90 cm.
- *Area of spread.*—About 30 cm.
- *Vigor.*—Moderately vigorous.
- *Branching habit.*—Freely basal branching; about four basal branches develop per plant.
- *Stems.*—Length: About 90 cm. Diameter: About 2 mm. Internode length: About 4 cm. Texture: Smooth. Color: 143A.
- *Foliage description.*—Leaves simple, opposite, generally symmetrical, durable and long persisting.

Length: About 11 cm. Width: About 4 cm. Shape: Elliptic. Apex: Acute. Base: Attenuate. Margin: Entire. Texture, both surfaces: Leathery; slightly rugose; glabrous. Venation pattern: Pinnate. Color: Variegated with irregular central green patterns surrounded by irregular pale yellow patterns extending towards margins. Young foliage, upper surface: Center, 189A; margins, 10A to 11A. Young foliage, lower surface: Center, 191A; margins, 11B. Mature foliage, upper surface: Center, 189A; margins, 11C to 11D. Mature foliage, lower surface: Center, 189A to 191A; margins, 11D. Venation, both surfaces: Same color as lamina. Petiole: Length: About 3 mm. Diameter: About 2 mm. Texture, both surfaces: Smooth. Color, both surfaces: 143B.

Flower description:

*Flower type and habit.*—Single salverform white-colored flowers with pink corolla tubes arranged in upright panicles; flowers face upward and outward. Flowers not persistent.

*Natural flowering season.*—Flowering continous during the summer from June to early September in Den Hoorn, The Netherlands.

*Quantity.*—Freely flowering with about 250 open flowers and flower buds per flowering stem over the entire flowering period.

*Fragrance.*—Moderate to faint; pleasant sweet fragrance, typical of species.

*Flower longevity on the plant.*—About 6 days.

*Flower longevity as a cut flower.*—About 10 to 14 days.

*Flower buds, about two days before opening.*—Length: About 1.7 cm. Diameter: About 4 mm. Shape: Ovate. Color: 157C to 157D.

*Corolla.*—Arrangement: Five-parted, petals fused at base into a slender tube, salverform. Flower diameter: About 3 cm. Flower height: About 2 cm. Flower tube length: About 2 cm. Petal length from throat: About 1.5 cm. Petal width: About 1.5 cm. Petal shape: Beyond tube, flabellate. Petal apex: Rounded. Petal margin: Entire. Texture: Smooth, velvety; tube, sparsely covered with short, less than 0.5 mm, whitish hairs. Petal color: When opening, upper and lower surfaces: 155C. Opened flower, upper and lower surfaces: 155C. Throat: 186B to 186C. Tube: 186B to 186C.

*Calyx.*—Calyx length: About 2 cm. Calyx diameter: About 3 mm. Sepal arrangement: Five fused at base, campanulate. Sepal shape: Linear. Sepal apex Acuminate. Sepal margin: Entire. Sepal texture, both surfaces: Smooth. Sepal color: Upper surface: 143B. Lower surface: 143B to 143C.

*Peduncle.*—Angle: Upright to about 65° from stem. Strength: Moderate. Length: About 3 to 4 mm. Diameter: Less than 1 mm. Color: 143B to 143C.

*Reproductive organs.*—Stamens: Stamen quantity/arrangement: Five, adnate to corolla tube. Anther shape: Elliptic to ovate; basifixed. Anther length: About 1 mm. Anther color: Pale yellowish green. Pollen amount: Moderate. Pollen color: Pale yellowish green. Pistils: Pistil quantity: One. Pistil length: About 1.4 cm. Stigma shape: Three-parted. Stigma color: 157A to 145D. Style length: About 1.3 cm. Style color: 145D. Ovary color: 141B to 141C.

*Seed.*—Seed production has not been observed.

Disease/pest resistance: Resistance to pathogens or pests common to Phlox has not been observed.

It is claimed:

1. A new and distinct cultivar of Phlox plant named 'Silvermine', as illustrated and described.

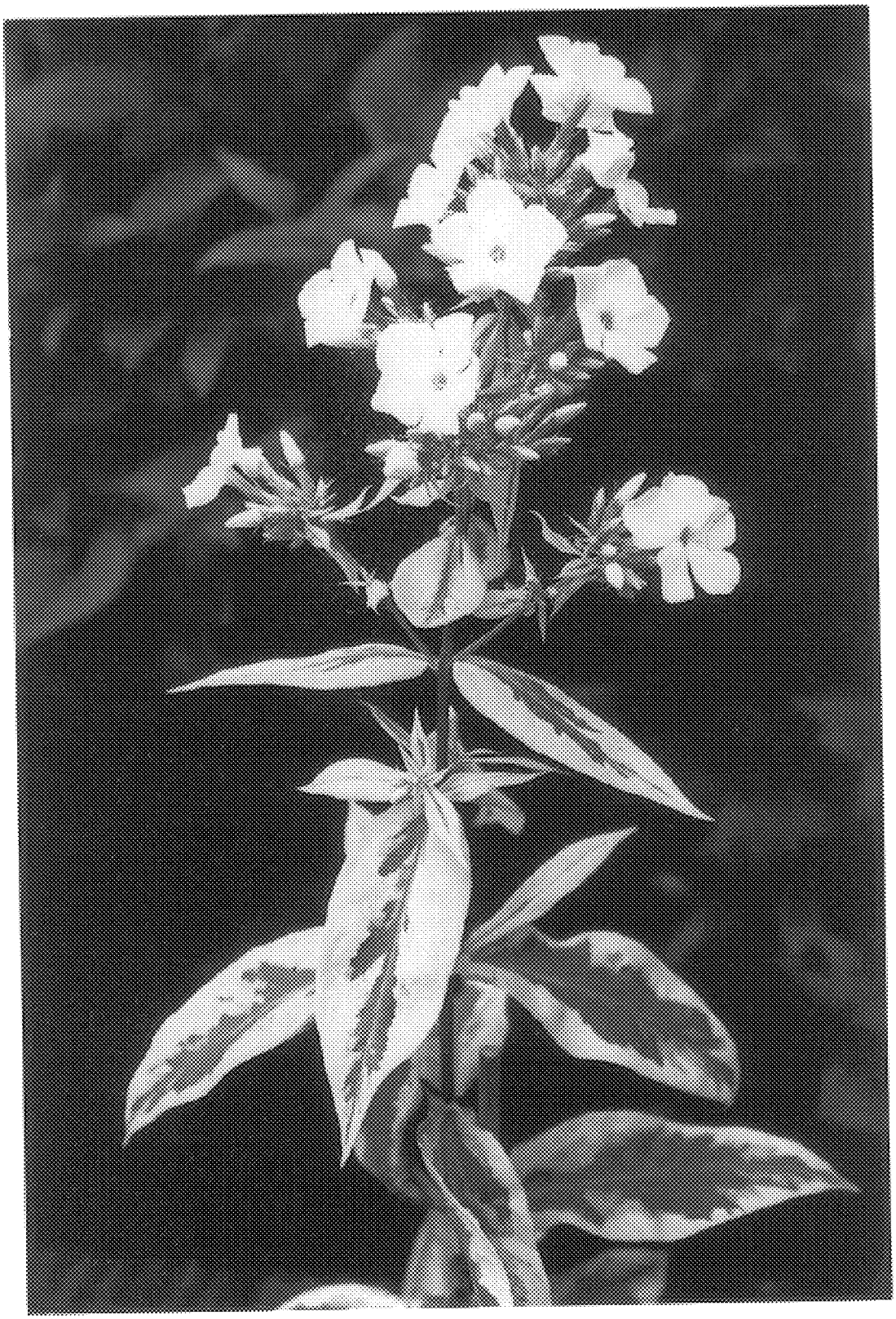

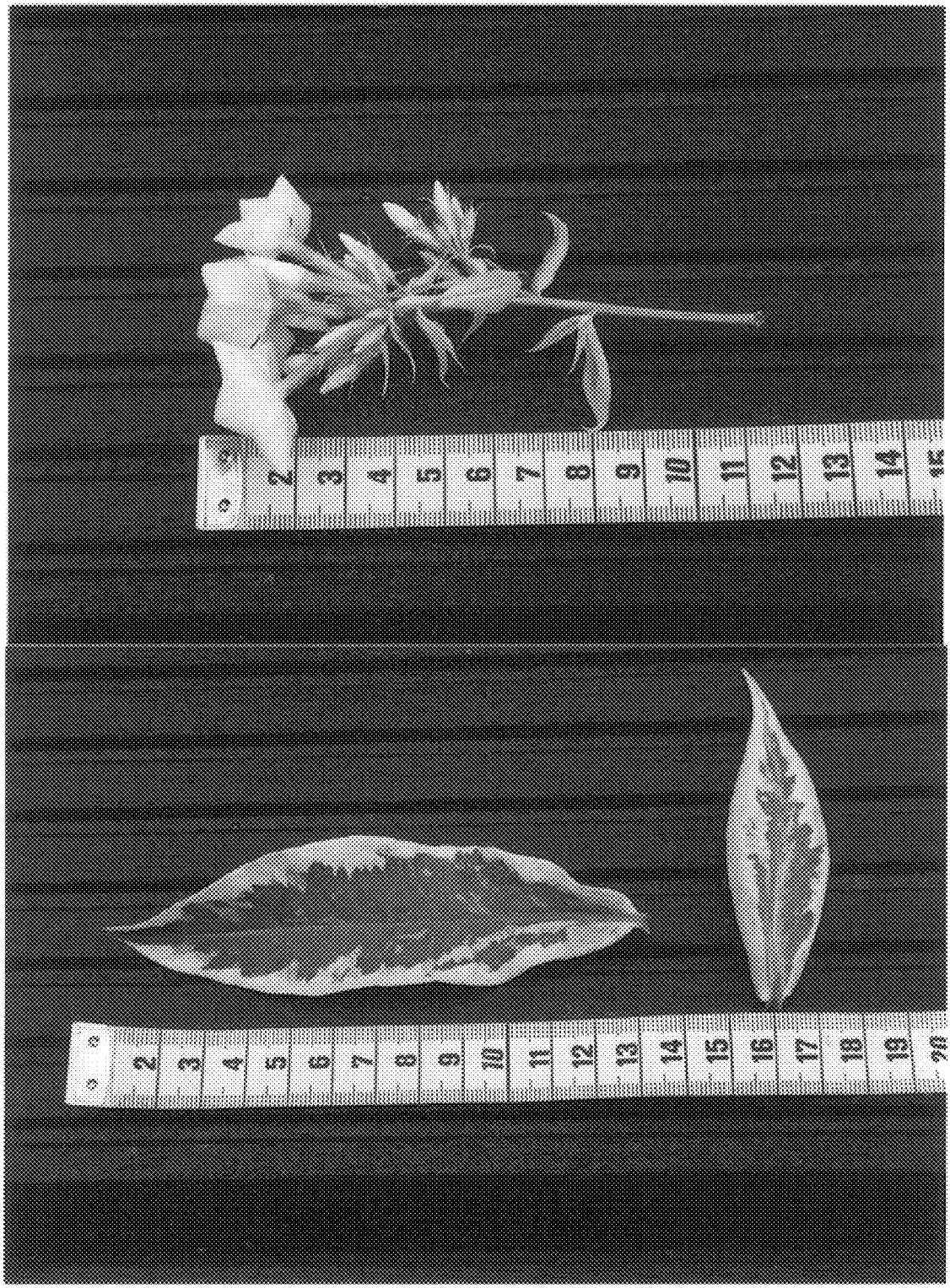

* * * * *